(12) United States Patent
Kelson et al.

(10) Patent No.: US 11,666,782 B2
(45) Date of Patent: *Jun. 6, 2023

(54) TREATMENT PLANNING FOR ALPHA PARTICLE RADIOTHERAPY

(71) Applicant: Alpha Tau Medical Ltd., Tel Aviv (IL)

(72) Inventors: Itzhak Kelson, Tel Aviv (IL); Lior Arazi, Tel Aviv (IL); Amnon Gat, Matan (IL)

(73) Assignee: ALPHA TAU MEDICAL LTD., Jerusalem (IL)

( * ) Notice: Subject to any disclaimer, the term of this patent is extended or adjusted under 35 U.S.C. 154(b) by 194 days.

This patent is subject to a terminal disclaimer.

(21) Appl. No.: 17/141,251

(22) Filed: Jan. 5, 2021

(65) Prior Publication Data

US 2022/0212035 A1 Jul. 7, 2022

(51) Int. Cl.
*A61N 5/10* (2006.01)
*G16H 20/40* (2018.01)
(Continued)

(52) U.S. Cl.
CPC .......... *A61N 5/1038* (2013.01); *A61N 5/1065* (2013.01); *G16H 20/40* (2018.01);
(Continued)

(58) Field of Classification Search
CPC .......... A61N 5/10; G16H 20/40; G16H 50/50; G16H 70/60; G16H 30/20
See application file for complete search history.

(56) References Cited

U.S. PATENT DOCUMENTS 8,834,837 B2 9/2014 Kelson et al.
8,894,969 B2 11/2014 Kelson et al.
(Continued)

FOREIGN PATENT DOCUMENTS

WO 2019161135 A1 8/2019
WO 2019235841 A1 12/2019

OTHER PUBLICATIONS

A Popovtzer, E Rosenfeld, R Ben-Hur, A Mizrachy, I Kelson, and Y Keisari. "A New Radiation Concept, Treatment of Squamous Cell Carcinoma by Alpha-radiation Based Brachytherapy (Alpha DaRT)". International Journal of Radiation Oncology*Biology* Physics, 2018, 102.3:e275. (Year: 2018).*

(Continued)

*Primary Examiner* — Christine H Matthews
*Assistant Examiner* — Joshua Daryl D Lannu
(74) *Attorney, Agent, or Firm* — Kliger & Associates Patent Attorneys Ltd (57) ABSTRACT

Apparatus for planning a diffusing alpha-emitter radiation therapy (DaRT) treatment session. The apparatus includes an output interface and a memory configured with a plurality of tables which provide an accumulated measure of radiation over a specific time period, due to one or more types of DaRT radiotherapy sources which emit daughter radionuclides from the source, for a plurality of different distances and angles relative to the DaRT radiotherapy source. In addition, a processor is configured to receive a description of a layout of a plurality of DaRT radiotherapy sources in a tumor, to calculate a radiation dose distribution in the tumor responsive to the layout, using the tables in the memory, and to output feedback for the treatment responsive to the radiation dose distribution, through the output interface.

24 Claims, 2 Drawing Sheets

(51) Int. Cl.
    *G16H 50/50*     (2018.01)
    *G16H 70/60*     (2018.01)
    *G16H 30/20*     (2018.01)
    *G01T 1/02*     (2006.01)

(52) U.S. Cl.
    CPC ............. *G16H 30/20* (2018.01); *G16H 50/50* (2018.01); *G16H 70/60* (2018.01); *A61N 2005/1041* (2013.01); *A61N 2005/1087* (2013.01); *G01T 1/02* (2013.01)

(56) References Cited

U.S. PATENT DOCUMENTS

| | | |
|---|---|---|
| 2002/0046010 A1 | 4/2002 | Wessol et al. |
| 2007/0084474 A1 | 4/2007 | Rivard |
| 2009/0182187 A1 | 7/2009 | Chaswal et al. |
| 2011/0184283 A1 | 7/2011 | Rivard |
| 2013/0165732 A1 | 6/2013 | Sgouros et al. |
| 2014/0018607 A1* | 1/2014 | Maier ................. A61N 5/1039 600/8 |
| 2019/0099620 A1 | 4/2019 | Isola et al. |

OTHER PUBLICATIONS

Arazi, "Diffusing Alpha-Emitters Radiation Therapy: Theoretical and Experimental Dosimetry," Ph.D. Thesis, Raymond and Beverly Sackler Faculty of Exact Sciences, School of Physics and Astronomy, Tel Aviv University, pp. 1-285, Sep. 2008.

Arazi et al., "Treatment of Solid Tumors by Interstitial Release of Recoiling Short-Lived Alpha Emitters," Physics in Medicine and Biology, vol. 52, issue 16, pp. 5025-5042, Aug. 1, 2007.

Arazi et al., "The Treatment of Solid Tumors by Alpha Emitters Released from 224Ra-Loaded Sources—Internal Dosimetry Analysis," Physics in Medicine and Biology, vol. 55, issue 4, pp. 1203-1218, Feb. 2, 2010.

Arazi, "Diffusing Alpha-Emitters Radiation Therapy: Approximate Modeling of the Macroscopic Alpha Particle Dose of a Point Source," Physics in Medicine and Biology, vol. 65, issue 1, 24 pages, year 2020.

Nath et al., Recommendations of the AAPM Radiation Therapy Committee Task Group No. 43, Medical Physics, vol. 22, issue 2, pp. 209-234, Feb. 1995.

Rivard et al., "Update of AAPM Task Group No. 43 Report: A Revised AAPM Protocol for Brachytherapy Dose Calculations," Medical Physics, vol. 31, issue 3, pp. 633-674, Mar. 2004.

International Application # PCT/IB2021/061607 Search Report dated Apr. 4, 2022.

Popovtzer et al., "A New Radiation Concept, Treatment of Squamous Cell Carcinoma by Alpha-Radiation Based Brachytherapy (Alpha DaRT)," International Journal of Radiation Oncology—Biology—Physics, vol. 102, No. 3S, supplement 2018, p. E275, year 2018.

International Application # PCT/IB2021/050034 Search Report dated Apr. 29, 2021.

U.S. Appl. No. 17/497,937 Office Action dated Sep. 16, 2022.

* cited by examiner

TREATMENT PLANNING FOR ALPHA PARTICLE RADIOTHERAPY

FIELD OF THE INVENTION

The present invention relates generally to radiotherapy and particularly to methods of selecting radiotherapy parameters.

BACKGROUND OF THE INVENTION

Alpha particles are a powerful means for radiotherapy of certain types of tumors, including malignant tumors. One type of alpha radiotherapy sources are diffusing alpha-emitter radiation therapy (DaRT) sources, also referred to herein as alpha-DaRT sources, loaded with radium-224 atoms, which have a half-life which is not too long and not too short for therapeutic purposes.

U.S. Pat. No. 8,834,837 to Kelson describes a method of DaRT treatment.

In order for treatment of a tumor to be effective, brachytherapy seeds employed in the treatment should release a sufficient number of particles to destroy the tumor. On the other hand, the seeds should not release an overdose of particles, as that could damage healthy tissue of the patient.

US patent publication 2013/0165732 to Sgouros et al. describes a computerized system for determining an optimum amount of radiopharmaceutical therapy (RPT) to administer.

The TG-43 publication (Recommendations of the AAPM Radiation Therapy Committee Task Group No. 43, Med. Phys. 22: 209-234) defines necessary physical quantities (e.g., air kerma strength, radial dose function, anisotropy function, dose rate constant, and the like) for the calculation of quantitative dosimetric data, for various interstitial brachytherapy sources.

US patent publication 2019/0099620 suggests adapting a radiotherapy treatment plan on the basis of a set of influence parameters quantifying an influence of the radiation on the target region per unity intensity emission in accordance with an anatomical configuration of the target region.

US patent publication 2011/0184283 describes brachytherapy treatment planning systems (TPS) which use Monte Carlo methods and calculate dose to a specific tissue type.

SUMMARY OF THE INVENTION

An aspect of some embodiments of the invention relates to a method for selecting parameters of a diffusing alpha-emitter radiation therapy, comprising calculating a dose distribution for a tumor radiotherapy, and adjusting the parameters based on the dose distribution.

There is therefore provided in accordance with embodiments of the present invention, apparatus for planning a diffusing alpha-emitter radiation therapy (DaRT) treatment session, comprising an output interface, a memory configured with a plurality of tables which provide an accumulated measure of radiation over a specific time period, due to one or more types of DaRT radiotherapy sources which emit daughter radionuclides from the source, for a plurality of different distances and angles relative to the DaRT radiotherapy source and a processor configured to receive a description of a layout of a plurality of DaRT radiotherapy sources in a tumor, to calculate a radiation dose distribution in the tumor responsive to the layout, using the tables in the memory, and to output feedback for the treatment responsive to the radiation dose distribution, through the output interface.

Optionally, the memory is configured with a plurality of tables for different time periods for a single source type, and wherein the processor is configured to determine a treatment duration of the layout, and to select tables to be used in calculating the radiation dose distribution responsive to the treatment duration. Optionally, the memory is configured with a plurality of tables for sources of a single source type in different zones of the tumor, and wherein the processor is configured to select tables to be used in calculating the radiation dose from each source in the layout, responsive to the zone in which the source is located. Optionally, the processor determines the zone in which a source is located responsive to a distance between the source and an edge of the tumor. Optionally, the processor is configured to identify areas of the tumor for which the dose is below a threshold and to suggest changes to the layout which bring the radiation dose in the identified areas to above the threshold.

Optionally, the processor is configured to repeat the calculation of radiation dose distribution for a plurality of different treatment durations and to select one of the durations responsive to the calculations. Optionally, the accumulated measure of radiation provided by the table comprises an accumulated radiation dose due only to alpha radiation.

Optionally, the accumulated measure of radiation provided by the table comprises an accumulated radiation dose due to alpha radiation and one or more of electron and photon radiation. Optionally, the accumulated measure of radiation provided by the table comprises one or more number densities of radionuclides.

There is further provided in accordance with embodiments of the present invention, a method of planning a radiotherapy treatment session, comprising receiving, by a processor, a description of a layout of a plurality of DaRT radiotherapy sources in a tumor, calculating, by the processor, a radiation dose distribution in the tumor responsive to the layout, using tables which provide an accumulated measure of radiation over a specific time period, due to one or more types of DaRT radiotherapy sources which emit daughter radionuclides from the source, for a plurality of different distances and angles relative to the DaRT radiotherapy source, and outputting from the processor feedback for the treatment responsive to the radiation dose distribution.

Optionally, calculating the radiation dose distribution comprises determining a treatment duration of the layout, and select tables to be used in calculating the radiation dose distribution responsive to the treatment duration. Optionally, calculating the radiation dose distribution comprises selecting tables to be used in calculating the radiation dose from each source in the layout, responsive to a zone of the tumor in which the source is located. Optionally, the method includes repeating the calculation of radiation dose distribution for a plurality of different treatment durations and selecting one of the durations responsive to the calculations.

There is further provided in accordance with embodiments of the present invention, a method of planning a radiotherapy treatment session, comprising receiving, by a processor, a plurality of parameters of tissue of a tumor requiring radiotherapy, receiving, by the processor, an indication of a layout of diffusing alpha-emitter radiation therapy (DaRT) sources to be placed in the tumor, calculating a distribution of radon-220, lead-212 and bismuth-212 radionuclides in the tumor, responsive to the layout of sources, determining a distribution of a dose resulting from alpha radiation emitted in the tumor responsive to the calculated distribution, determining an electron and a photon radiation dose distribution in the tumor, responsive to the sources; and setting one or more parameters of the radiotherapy treatment session responsive to the determined distributions of the alpha, electron and photon radiation.

Optionally, calculating the distribution of radon-220, lead-212 and bismuth-212 is performed as a function of diffusion coefficients of radon-220 and lead-212 in the tumor. Optionally, calculating the distribution of radon-220, lead-212 and bismuth-212 is performed by solving a migration equation of lead-212 including a leakage factor which is a product of the concentration of lead-212 and a constant. Optionally, calculating the distribution of the radionuclides comprises calculating a distribution of the radionuclides for a single source and summing the distributions of the sources in the layout.

Optionally, the setting one or more parameters of the radiotherapy treatment session comprises selecting an activity of the sources. Optionally, the setting one or more parameters of the radiotherapy treatment session comprises adjusting the layout of the sources. Optionally, calculating the distribution of radon-220, Lead-212 and bismuth-212 in the tumor and determining the distribution of alpha radiation comprises preparing in advance tables of radiation distributions for a plurality of different tumor types and calculating the distribution of alpha radiation by summing values matching the layout from one of the tables. Optionally, preparing in advance tables of radiation distributions comprises preparing for each of the tumor types, a plurality of tables for respective treatment durations. Optionally, the treatment durations for which the tables are prepared, are unevenly distributed over the duration of the effectiveness of the sources of the layout. Optionally, calculating the distribution of radionuclides in the tumor and determining the distribution of alpha radiation comprises repeating the determination for a plurality of different durations, and wherein setting one or more parameters of the radiotherapy treatment session comprises selecting a duration of the treatment responsive to the repeated determinations.

Optionally, receiving the indication of the layout comprises receiving an image of the tumor with the sources therein and determining the locations of the sources in the tumor responsive to the image. Optionally, determining the electron and the photon radiation dose distribution, is performed in a manner ignoring the distribution of radon-220, lead-212 and bismuth-212 in the tumor. Optionally, calculating the distribution of radon-220, lead-212 and bismuth-212 radionuclides comprises calculating based on at least one equation which depends and a diffusion coefficient of lead-212, and wherein the value of the diffusion coefficient of lead-212 is calculated as a function of a diffusion length of lead-212. Optionally, the diffusion length of lead-212 is assigned a value in the range of 0.2-0.4 millimeters. Optionally, the diffusion length of lead-212 is assigned a value dependent on the tissue type of the tumor.

DETAILED DESCRIPTION OF EMBODIMENTS

An aspect of some embodiments of the present invention relate to the use of pre-calculated tables of the radiation distribution due to a radiotherapy source, in calculating an estimated radiation amount resulting from an alpha-DaRT source, which emits daughter radionuclides into a treated tumor. The tables provide, for a plurality of positions relative to the source, an accumulated radiation dose at the position.

In some embodiments, separate tables, or table entries, are used for different time periods of radiotherapy treatment.

In some embodiments, separate tables are provided for different areas within the tumor, for example according to distance from the edge of the tumor.

Using tables which indicate the accumulated dose over a treatment period, overcomes the problem that the spatial distribution of radionuclides is time dependent and cannot be factorized into a time dependent and spatial dependent component. In addition, use of the dose in the tables avoids the problem that for DaRT the dose rate at t=0 is 0, increases with time and then decreases.

Figure 1:
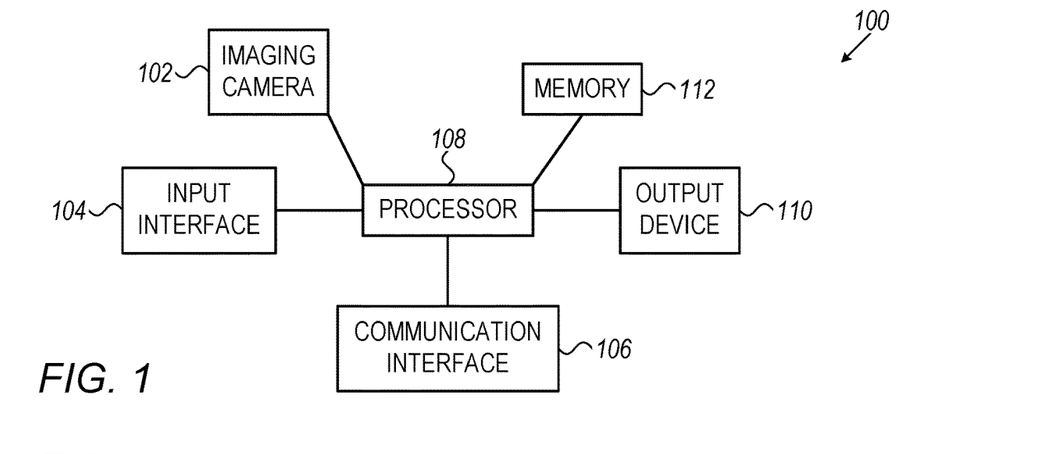
FIG. 1 is a schematic illustration of a system for planning a radiotherapy treatment, in accordance with an embodiment of the present invention.

FIG. 1 is a schematic illustration of a system 100 for planning a radiotherapy treatment, in accordance with an embodiment of the present invention. The treatment generally includes implantation of a plurality of sources in a tumor which is to be destroyed. The sources, also known as "seeds", generally comprise a base coated by radium-224 as described, for example, in U.S. Pat. No. 8,894,969, which is incorporated herein by reference. The base may have any suitable shape, such as a thin cylinder shape.

System 100 comprises an imaging camera 102 which acquires images of tumors requiring radiotherapy. In addition, system 100 includes an input interface 104, such as a keyboard and/or mouse, for receiving input from a human operator, such as a physician. Alternatively or additionally, system 100 comprises a communication interface 106 for receiving instructions and/or data from a remote computer or human operator. System 100 further comprises a processor 108 configured to generate a layout plan of radiotherapy sources in the tumor. Processor 108 is further configured to estimate the radiation dose expected to reach each of the points in the tumor, and accordingly to provide an output to the human operator through an output device 110, such as a computer screen.

Processor 108 is coupled to a memory 112 which preferably stores tables of radiation doses as a function of distance, and optionally also angle, from the source. The tables are calculated in advance for different types of sources and parameters of the tumor tissue, as discussed hereinbelow.

Figure 2:
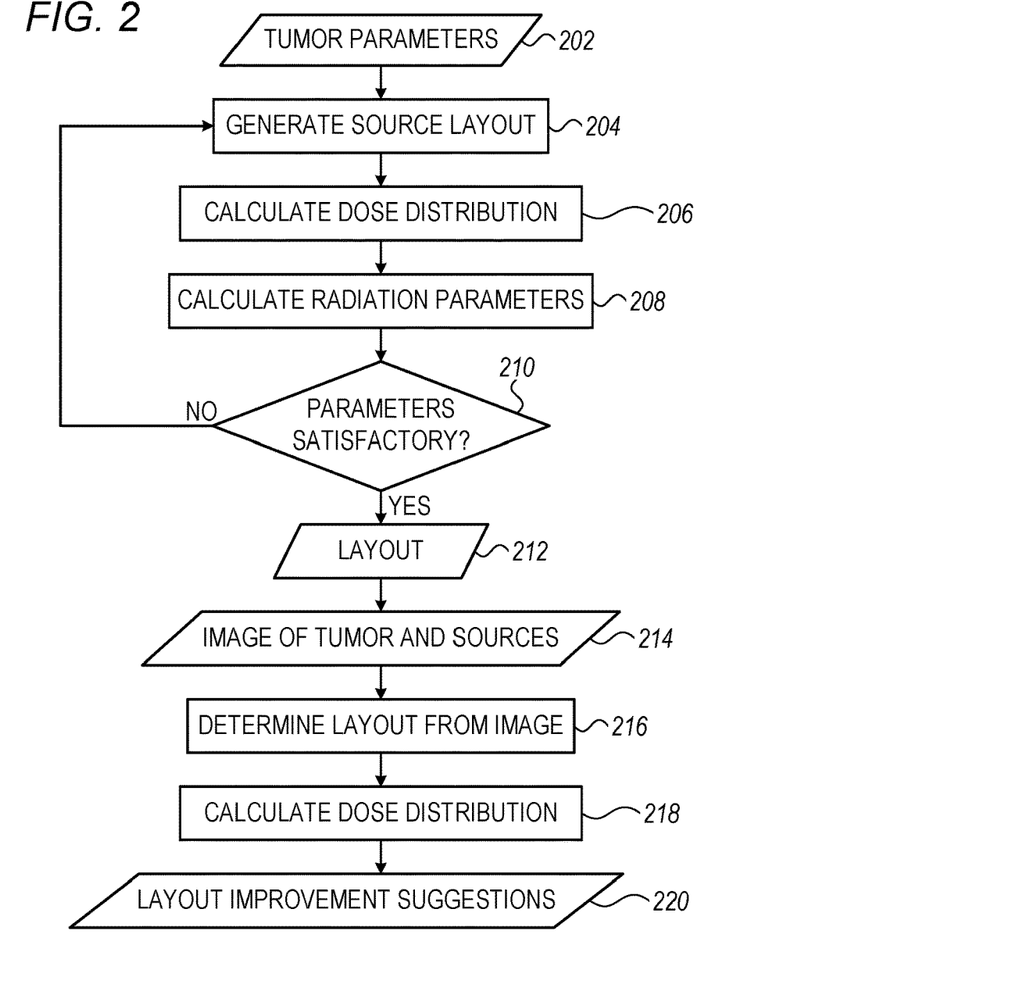
FIG. 2 is a flowchart of acts of a method of calculating a dose distribution for a tumor radiotherapy, in accordance with an embodiment of the invention.

FIG. 2 is a flowchart of acts performed by system 100, in accordance with an embodiment of the invention. System 100 receives (202) input on the tumor and a layout of radiotherapy sources for the tumor is generated (204). The layout optionally includes, in addition to relative positions of the sources, information on the sources (e.g., the activity level of the sources) and a time of treatment.

Processor 108 calculates (206) a dose distribution of the radiation from the sources of the layout and/or calculates (208) any other parameters of the radiation of the sources, such as a dose volume histogram and/or a dose-rate distribution. In some embodiments, a determination (210) is made as to whether the dose distribution and/or other parameters are satisfactory, and if not satisfactory, a new layout is generated (204) and the calculation of the dose distribution and/or the other parameters of the radiation are repeated for the new layout. The generation (204) of layouts and calculation of dose distribution (206) and/or the other parameters (208) is optionally repeated until a suitable layout is identified and provided (212) for insertion of the sources into the tumor.

In some embodiments, the determination (210) as to whether the dose distribution and/or other parameters are satisfactory, and the generation of the new layout are performed by a human operator. Alternatively, processor 108 automatically determines (210) whether the dose distribution is sufficient, for example by determining areas of the tumor where the radiation is below a first threshold. The first threshold is optionally selected responsive to the type of the tumor, for example the nucleus size of the cells of the tumor. In some embodiments, processor 108 automatically determines a percentage of the tumor to which the radiation dose is above the first threshold and compares this percentage to a second threshold. The generation (204) of the new layout is optionally performed automatically by moving sources from areas where the radiation is substantially above the first threshold, to areas where the radiation dose is below the first threshold. Alternatively or additionally, the automatic generation of the new layout is performed by adding additional sources.

In some embodiments, after the sources are inserted into the tumor, an image of the tumor with the sources is acquired (214) and the actual layout of sources in the tumor is determined (216). Processor 108 then optionally calculates (218) a dose distribution of the radiation from the sources of the actual layout and if necessary provides (220) suggestions for improvement of the layout.

The suggestions (220) for improvement of the layout and the generation (204) of the new layout, may include adding sources to be inserted to the tumor, removal of unnecessary sources, moving one or more sources in the layout (e.g., changing the spacings between sources), changing the activity and/or desorption probability of one or more of the sources and/or changing the types or sizes of the sources.

In some embodiments, the layout is generated (204) automatically by processor 108 by distributing sources throughout the tumor in a default spacing for the specific tumor type. Alternatively or additionally, the layout is generated with a spacing indicated by the human operator. Further alternatively or additionally, a human operator indicates locations of the sources through input interface 104, on a displayed image of the tumor. The layout optionally also includes an indication of one or more properties of the sources used in the layout, such as the length of the sources and/or their activity level (i.e., the amount of radioactive atoms on the sources). The information on the sources may be provided by a human user or may be selected by processor 108 automatically, for example based on default values, or based on a code number provided by the human operator. In some embodiments, processor 108 determines the properties of the sources from an image of the tumor, with the sources therein, in cases in which the analysis is of sources already implanted. The sources may include, in these embodiments, markings of their type and/or properties, which are easily determinable from images of the tumor.

The information on the layout optionally also includes a duration for which the analysis is performed, for example, the amount of time the sources are planned to be in the tumor, or an amount of time for which the sources were in the patient if the analysis is performed after the treatment was completed. In some embodiments of the invention, the calculation is performed for a plurality of different durations, in order to select a duration most suitable for the treatment. For example, the calculation may be performed during the treatment to determine when to remove the sources.

The calculation (206) of the dose distribution is based, in some embodiments, on pre-generated tables stored in memory 112. The calculation (206) optionally includes selecting one of the tables in memory 112, responsive to the type of the tissue of the tumor and the type of the sources used in the layout. For each type of tissue, the tables are calculated in advance as described below with reference to FIG. 3. Each table optionally indicates, for a plurality of locations relative to the source type of the table, an amount of radiation reaching the location, per unit of activity of the source. The locations are optionally designated by an angle ($\theta$) and distance (r) from a center of the source. The table includes, for example, 90 rows representing possible angles in a granularity of 2° in the range of 0°-180°, and 100 columns of distances from 0 to 10 millimeters in a granularity of 0.1 millimeter. These numbers of rows and columns are provided by way of example and larger or smaller tables with coarser or finer granularities are also to be considered in the scope of the present invention. For example, the table may include 180 rows for a 1° granularity. In some embodiments, dose values in the tables are provided in units of gray. In other embodiments, the values in the table are of dose per initial release rate of radon, for example in units of gray to micro-Curie.

The tables described herein may be stored in memory 112 in any suitable data structure. Each table may be stored, for example, in a single array, or in a plurality of arrays. Each of the tables may be stored separately, or a plurality of tables may be stored together as a single table, of a larger dimension.

In calculation (206) of the dose distribution, for each location of interest (e.g., the locations in the tumor, and possibly also adjacent the tumor), processor 108 checks the table for the radiation dose received from each of the sources per unit activity of the source, and multiplies this value by the activity of the source. These values are summed to provide the total radiation dose reaching the point. Alternatively to multiplying by the activity of the sources, the doses from the table are multiplied by the release rate of radon from the source.

In some embodiments, in which all the sources have the same activity, the multiplication by the activity or by the release rate of radon of the sources may be performed after the summation.

Alternatively or additionally, separate tables are provided for each activity level (or release rate of radon), and the tables provide values of activity or release rate of radon, such that the multiplication is not required.

In some embodiments, for each tissue type, a plurality of tables are provided for different treatment durations. For example, tables are optionally provided for a span of equally distanced durations with a granularity of one day or two days. Alternatively, the tables are prepared for unevenly distributed durations, for which the calculated doses are sufficiently different to warrant an additional table. In selecting the table to be used for a specific source, the duration of the treatment is also considered. In some embodiments, when a treatment duration is between the durations of two different tables, the values from both tables are retrieved and the actual value is calculated from the table values by interpolation. Alternatively, in cases in which the treatment is expected to always be for a relatively long duration, a single table of a long duration, greater than several half-lives of radium-224, is used.

In other embodiments, the tables indicate other parameters from which the dose may be calculated relatively easily. For example, the tables provide, in some embodiments, a number of accumulated decays of two or more radionuclides involved in the treatment, for each of the positions relative to the source. The radiation dose is calculated from the values in the table by first determining the number of accumulated decays of the radionuclides involved in the treatment not included in the table, and then calculating the dose from the numbers of accumulated decays. The calculation of the radiation dose from the numbers of accumulated decays may be performed before or after the summation of the effect of all the sources in the layout. Optionally, the two or more radionuclides whose number of accumulated decays are included in the tables are radon-220 and bismuth-212. Alternatively to radon-220, the number of accumulated decays of polonium-216 is given. Further alternatively or additionally, instead of for bismuth-212, the number of accumulated decays in the tables may be of lead-212, polonium-212 and/or thallium-208. In some embodiments, the table may give the number of accumulated decays for more than two or even more than three of the radionuclides, possibly even of all the radionuclides involved in the treatment.

In some embodiments, the type of the tumor is determined based on clinical and/or histopathological observations, such as an analysis of a portion of the tumor taken in a biopsy. The type of the tumor is selected, for example, from a list including squamous cell carcinoma, basal cell carcinoma, glioblastoma, sarcoma, pancreatic cancer, lung cancer, prostate cancer, breast cancer and colon cancer. This list of tumor types is provided merely as one example and tables may be prepared for larger or smaller lists of tumor types including all or some of the above listed types and/or other types not listed here.

Figure 3:
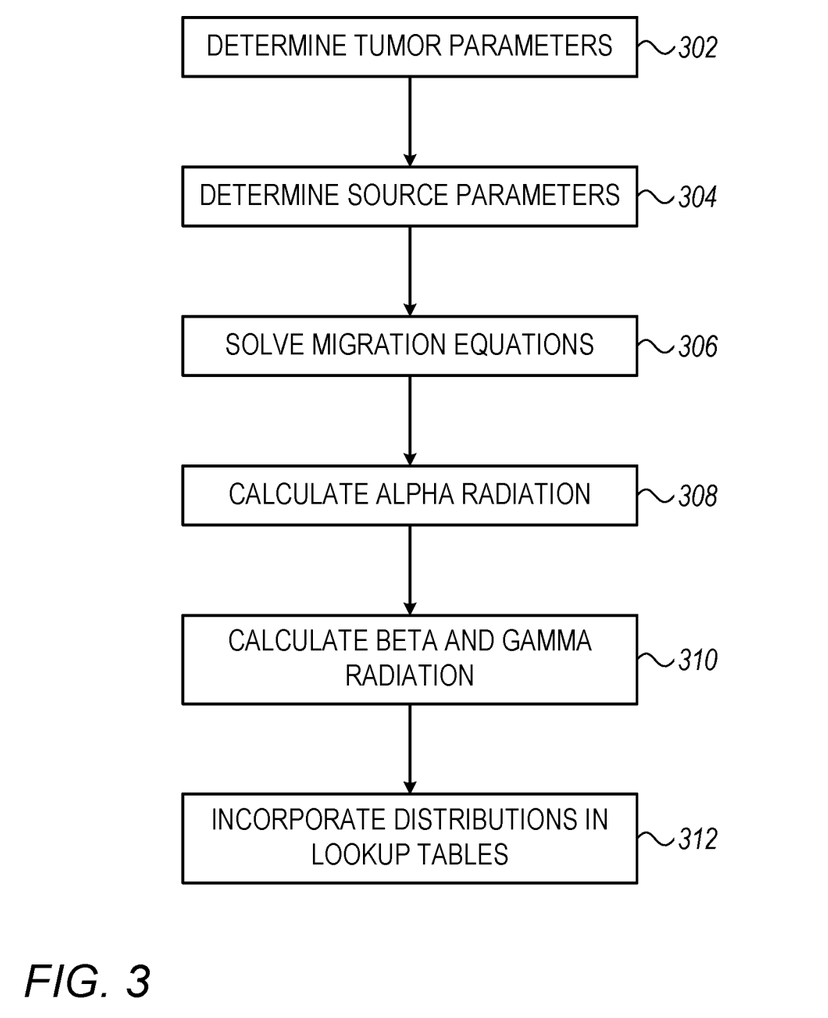
FIG. 3 is a schematic illustration of acts performed in generating the tables in memory, in accordance with an embodiment of the invention.

FIG. 3 is a schematic illustration of acts performed in generating the tables in memory 112, in accordance with an embodiment of the invention. The method optionally includes determining (302) one or more tissue specific parameters which represent the diffusion of radioactive isotopes from the sources in tumors of different types of cancers to be treated. Optionally, the parameters include diffusion coefficients $D_{Rn}$, $D_{Pb}$ and $D_{Bi}$ of the isotopes radon-220 ($^{220}$Rn), lead-212 ($^{212}$Pb) and bismuth-212 ($^{212}$Bi), respectively, in the different tumor types. Optionally, the diffusion coefficients $D_{Rn}$, $D_{Pb}$ and $D_{Bi}$ are measured using methods known in the art, such as described in Lior Arazi, "Diffusing Alpha-Emitters Radiation Therapy: Theoretical and Experimental Dosimetry", Thesis submitted to the senate of Tel Aviv University, September 2008, the disclosure of which is incorporated herein by reference, and/or in Lior Arazi et al., "Treatment of solid tumors by interstitial release of recoiling short-lived alpha emitters", Physics in Medicine & Biology, 2007, the disclosure of which is incorporated herein by reference.

In some embodiments, the diffusion coefficients $D_{Rn}$, $D_{Pb}$ and $D_{BL}$ are measured in mice or other test animals. While such measurements may not be totally accurate, due, for example, to convective effects, applicant has determined that even when these inaccuracies are ignored, the calculations achieve suitable results.

The tissue specific parameters optionally further include the parameters $\alpha_{Pb}$ and $\alpha_{Bi}$ which represent a leakage rate (assumed to be uniform throughout the tumor) of lead-212 and Bi-212 respectively due to leakage through the blood from the tumor. The leakage rate parameters $\alpha_{Pb}$ and $\alpha_{Bi}$ are optionally determined such that the mean leakage times (average time for $^{212}$Pb and $^{212}$Bi to leave the tumor through the blood) are $1/\alpha_{Pb}$ and $1/\alpha_{Bi}$.

In some embodiments, the value of $\alpha_{Pb}$ is determined from measured values of the lead-212 leakage probability. The lead-212 leakage probability is measured using any suitable method known in the art, such as measurement in mice as described in the above mentioned article of Lior Arazi et al., "Treatment of solid tumors by interstitial release of recoiling short-lived alpha emitters", Physics in Medicine & Biology, 2007. Alternatively or additionally, the value of $\alpha_{Pb}$ is inferred from activity measurements in blood and/or urine of human patients using a biokinetic model, for example as described in Lior Arazi et al., "The Treatment Of Solid Tumors By Alpha Emitters Released From $^{224}$Ra-Loaded Sources—Internal Dosimetry Analysis", Physics in Medicine and Biology, February 2010, the disclosure of which is incorporated herein by reference in its entirety.

Preclinical data gathered from samples of DaRT-treated tumors, indicated that $^{212}$Bi leakage from the tumor, independently of the leakage of $^{212}$Pb, is a small effect, which implies that $\alpha_{Bi} \ll \lambda_{Bi}$ (where $\lambda_{Bi}$ is the decay rate constant of bismuth-212). In addition, $^{212}$Bi was found to be in local transit equilibrium with $^{212}$Pb, which, in turn implies that $D_{Bi} \leq 0.2 D_{Pb}$. Accordingly, in some embodiments, it is assumed that $\alpha_{Bi}=0$ and $D_{Bi}=0.1 D_{Pb}$. Alternatively, $\alpha_{Bi}$ is inferred from measurements in mice-based experiments in which the ratio of the activities of Bi-212 and lead-212 is measured in small samples. Further alternatively, $\alpha_{Bi}$ is set to a product of $\alpha_{Bi}$ and a constant k smaller than 1, smaller than 0.25 or even not greater than 0.2, for example 0.2 or 0.1. $D_{Bi}$ is set in some embodiments as a product of $D_{Pb}$ and a constant $k_2$, where typically $k_2 < 1$.

The method further includes determining (304) parameters which represent the radiotherapy source. In some embodiments, the source is represented by: $\Gamma_{Ra}^{src}(0)$ which is the initial $^{224}$Ra activity of the source, $P_{des}$(Rn) which is an $^{220}$Rn desorption probability from the source (i.e., the probability that a $^{220}$Rn is emitted from the source when $^{224}$Ra decays) and $P_{des}^{eff}$(Pb) which is an effective desorption probability of $^{212}$Pb from the source, due to any of the possible $^{212}$Pb release paths from the source. Optionally, $P_{des}^{eff}$(Pb) takes into account two $^{216}$Po channels, as well as creation of $^{212}$Pb outside of the source following the emission of $^{220}$Rn from the surface of the source. These parameters are determined using any suitable method known in the art, such as any of the methods described in the above mentioned article: Lior Arazi, "Diffusing alpha-emitters radiation therapy: approximate modeling of the macroscopic alpha particle dose of a point source", Physics in Medicine and Biology, 2020.

Using the tissue specific parameters and the source parameters, equations of migration of each of the isotopes $^{220}$Rn, $^{212}$Pb and $^{212}$Bi, resulting from the source, are solved (306) to determine the spatial distributions of the isotopes $n_{Rn}(r,t)$, $n_{Pb}(r,t)$ and $n_{Bi}(r,t)$, as a function of time t and position r relative to the source. Generally, the position r is a three-dimensional vector, but in some cases, for simplicity, a simpler measure of position is used, for example based on symmetry considerations. Optionally, due to the short half-lives of $^{216}$Po, $^{212}$Po and $^{208}$Tl, these isotopes are assumed to be in local transit and/or secular equilibrium with their parent isotopes and do not require separate equations to calculate their spatial distributions.

The resulting alpha radiation dose from the determined spatial distributions of the isotopes is calculated (308). In addition, the electron (beta, Auger, conversion electron) and photon (gamma, x-ray) radiation dose from the source is calculated (310) using any suitable method known in the art. The calculated alpha, electron and photon radiation dose distributions D(r, θ, t) are optionally incorporated (312) into lookup tables for each set of parameters of tumor type and source type. Here, assuming axial symmetry, r designates the radial distance of the point of interest from the source center and θ designates the angle between the line connecting the point of interest to the source center and the source axis.

Migration Equations

In some embodiments, the radon migration equation (also referred to as a transport equation) is given by:

$$\frac{\partial n_{Rn}}{\partial t} + \nabla \cdot j_{Rn} = s_{Rn} - \lambda_{Rn} n_{Rn} \tag{1}$$

Where $$\frac{\partial n_{Rn}}{\partial t}$$

is a rate of change of the amount of radon, $n_{Rn}$ (r, t) is the local concentration (number density) of $^{220}$Rn atoms (in units of cm$^{-3}$), $S_{Rn}$(r, t) is the $^{220}$Rn source term (i.e., the amount of radon released into the tissue due to the decay of $^{224}$Ra) (in units of cm$^{-3}$ s$^{-1}$), and $\lambda_{Rn}$ is the decay rate constant $\lambda_{Rn}$=ln(2/$\tau_{1/2}$), where $\tau_{1/2}$ is the half-life constant of radon-220. Note that if $^{224}$Ra is completely confined to the source $S_{Rn}$(r, t)=0 in the tumor volume and the source term is replaced by a suitable boundary condition on the source surface describing the flux of emitted $^{220}$Rn atoms. The current density $j_{Rn}$(r, t) is the net vector flux of 220Rn atoms (in units of cm$^{-2}$ s$^{-1}$).

In the most general case, $j_{Rn}$(r, t) is composed of both diffusive and convective terms:

$$j_{Rn}(r,t) = -D_{Rn}(r,t)\nabla n_{Rn}(r,t) + n_{Rn}(r,t)v(r,t) \tag{2}$$

v(r,t) is a vector field describing both vascular and interstitial flow inside the tumor.

The Pb migration equation is optionally:

$$\frac{\partial n_{Pb}}{\partial t} + \nabla \cdot j_{Pb} = s_{Pb} - \lambda_{Pb} n_{Pb} \tag{3}$$

where $$j_{Pb}(r,t) = -D_{Pb}(r,t)\nabla n_{Pb}(r,t) + n_{Pb}(r,t)v(r,t) \tag{4}$$

The transport equation relating to the total $^{212}$Bi number density is optionally:

$$\frac{\partial n_{Bi}}{\partial t} + \nabla \cdot j_{Bi} = s_{Bi} - \lambda_{Bi} n_{Bi} \tag{5}$$

Where:

$$j_{Bi}(r,t) = -D_{Bi}(r,t)\nabla n_{Bi}(r,t) + n_{Bi}(r,t)v(r,t) \tag{6}$$

If $^{224}$Ra of a meaningful amount is present in the tumor away from the source, its number density $n_{Ra}$(r,t) can be found by solving a separate transport equation, and then used as a volumetric source term for $^{220}$Rn, with $s_{Rn}(r,t) = \lambda_{Ra} n_{Ra}(r,t)$.

The source terms $s_{Rn}$(r,t) and $s_{Pb}$(r,t) are optionally determined based on the given physical arrangement of the sources inside the tumor and with the appropriate flux boundary conditions on the source surfaces.

The above equations are solved (306) using any suitable method known in the art, such as Monte Carlo simulation describing the stochastic motion of $^{220}$Rn, $^{212}$Pb and $^{212}$Bi, or numerically using finite elements (for any source geometry, with appropriate boundary conditions). These solution methods are required if one considers the tumor as a heterogenic, and possibly time-dependent medium, where the diffusion coefficients and velocity field depend on space and time. Alternatively, approximate solutions can be obtained if the tumor is modeled as a homogeneous, isotropic, and time-independent medium. In this case, in addition to the solution methods mentioned above, one can also solve the transport equations approximately using closed-form expressions for simple geometries, such as the ideal point source, infinite line source or infinite cylinder, and/or infinite planar source. An example solution which may be used is described in Lior Arazi, "Diffusing alpha-emitters radiation therapy: approximate modeling of the macroscopic alpha particle dose of a point source", Physics in Medicine and Biology, 2020, the disclosure of which is incorporated herein by reference.

In some embodiments, the equations are solved by first preparing solutions for point sources, and then summing the effects of the point sources forming the actual geometries of the sources.

For a point source of $^{224}$Ra, the $^{220}$Rn source term is optionally:

$$s_{Rn}(r,t) = P_{des}(Rn)\Gamma_{Ra}^{src}(0)e^{-\lambda_{Ra}t}\delta(r) \tag{7}$$

where r is the radial distance from the source. $\Gamma_{Ra}^{src}(0)$ is the initial $^{224}$Ra activity (t=0 at the time of the procedure), which decays exponentially as $e^{-\lambda_{Ra}t}$; $P_{des}$(Rn) is the $^{220}$Rn desorption probability from the source (i.e., the probability that a $^{220}$Rn is emitted from the source when $^{224}$Ra decays), and δ(r) is the Dirac delta function.

The source term for $^{212}$Pb is optionally:

$$s_{Pb}(r,t) = \lambda_{Rn} n_{Rn} + [P_{des}^{eff}(Pb) - P_{des}(Rn)]\Gamma_{Ra}^{src}(0)e^{-\lambda_{Ra}t}\delta(r) \tag{8}$$

The first term represents the local creation of $^{212}$Pb by the decay of $^{220}$Rn through $^{216}$Po away from the source. The second term represents the emission of $^{212}$Pb from the source either by direct recoil, when $^{216}$Po decays on the source, or in the immediate vicinity of the source when $^{216}$Po which has previously recoiled out of the source decays. Note that $P_{dess}^{eff}$(Pb) is the effective desorption probability of $^{212}$Pb from the source which includes, in addition to two $^{216}$Po decay channels, also the creation of $^{212}$Pb outside of the source following the emission of $^{220}$Rn from the surface of the source. Since the contribution of $^{220}$Rn is already taken care of by the first term, $\lambda_{Rn} n_{Rn}$, in the second term we use the difference $P_{des}^{eff}$(Pb)−$P_{des}$(Rn).

It is optionally assumed that $^{212}$Bi enters the tumor only through decay of $^{212}$Pb away from the source and therefore the $^{212}$Bi source term in eq. (3) is:

$$s_{Bi}(r,t) = \lambda_{Pb} n_{Pb}(r,t) \tag{9}$$

In some embodiments, to cover diffusion of bismuth-212 from the source, when a source which allows such diffusion is used, a suitable boundary condition is added on the source.

Alternatively, for an ideal point source, a Dirac delta function term can be employed for bismuth-212, as used above for radon-220 and lead-212.

In some embodiments, the equations are simplified to reduce the complexity of their solution, based on one or more of the following assumptions:

- The tumor medium is homogenous, isotropic and time-independent. The diffusion and leakage rate coefficients are constant in space and time.
- $^{224}$Ra daughter migration inside the tumor is predominantly diffusive. Vascular convection by the tortuous capillaries is characterized by a short correlation length (relative to therapeutically significant distances) and is therefore assumed to be in random directions. Thus, it can be incorporated into an effective diffusion coefficient.
- The sources are assumed to remain fixed in place throughout the treatment.
- All sources are the same: same length, same activity, same desorption probabilities.
- $^{220}$Rn decays entirely inside the tumor.
- Interstitial convection is neglected.
- $^{212}$Pb migration can be described using a single effective diffusion coefficient representing the average over all $^{212}$Pb molecular species.
- $^{212}$Pb atoms reaching major blood vessels are trapped in red blood cells (RBCs) and quickly cleared from the tumor. This process is described by a uniform volumetric sink term. The finite clearance rate reflects the time it takes migrating $^{212}$Pb atoms to reach such traps.
- Since the short-lived $^{220}$Rn atoms are free to diffuse with no chemical interaction through blood vessels and RBCs, the equation for $^{220}$Rn does not include a sink term (i.e. blood vessels do not act as traps for $^{220}$Rn). However, in some embodiments, in blood-rich regions of the tumor a similar sink term can be added also to the equation of $^{220}$Rn.
- The diffusion equation for $^{212}$Bi includes a sink term. However, this is generally considered a second order effect.

Under this set of assumptions, the above equations may be simplified to:

$$\frac{\partial n_{Rn}}{\partial t} - D_{Rn}\nabla^2 n_{Rn} = s_{Rn} - \lambda_{Rn} n_{Rn} \tag{10}$$

$$\frac{\partial n_{Pb}}{\partial t} - D_{Pb}\nabla^2 n_{Pb} = s_{Pb} - \lambda_{Pb} n_{Pb} - \alpha_{Pb} n_{Pb} \tag{11}$$

$$\frac{\partial n_{Bi}}{\partial t} - D_{Bi}\nabla^2 n_{Bi} = s_{Bi} - \lambda_{Bi} n_{Bi} - \alpha_{Bi} n_{Bi} \tag{12}$$

In equations (10)-(12) $n_{Rn}(r,t)$, $n_{Pb}(r,t)$ and $n_{Bi}(r,t)$ are the local time-dependent number densities of $^{220}$Rn, $^{212}$Pb and $^{212}$Bi throughout the tumor. $D_{Rn}$, $D_{Pb}$ and $D_{Bi}$ are the effective diffusion coefficients of the three isotopes, which are assumed to be independent of the position and time. $\lambda_{Rn}$, $\lambda_{Pb}$ and $\lambda_{Bi}$ are the respective decay rate constants. The $^{212}$Pb and $^{212}$Bi equations contain sink terms $\alpha_{Pb} n_{Pb}$ and $\alpha_{Bi} n_{Bi}$ describing $^{212}$Pb and $^{212}$Bi leakage (i.e., removal from the tumor) through the blood.

As mentioned above regarding the general equations (1), (3), (5), equations (10)-(12) are solved (306) using any suitable method known in the art, such as Monte Carlo simulation describing the stochastic motion of $^{220}$Rn, $^{212}$Pb and $^{212}$Bi, numerically using finite elements (for any source geometry, with appropriate boundary conditions), or approximately using closed-form expressions for simple geometries, such as the ideal point source, infinite line source or infinite cylinder, and/or infinite planar source.

In some embodiments, for simplicity, instead of solving migration equations for all three of $^{220}$Rn, $^{212}$Pb and $^{212}$Bi, one or more of the radionuclides is assumed to have a fixed distribution or a distribution dependent on one or more of the other radionuclides. For example, in one embodiment, the calculation of the dose is calculated based on the migration equation of $^{212}$Pb and the distribution of $^{220}$Rn is considered negligible and the distribution of $^{212}$Bi is assumed to be a fixed function of the $^{212}$Pb distribution. Alternatively, one solves the equations for $^{220}$Rn and $^{212}$Pb, and the $^{212}$Bi number density is assumed to be proportional to that of $^{212}$Pb (e.g., in transit or secular equilibrium).

Alpha Dose Calculation

The alpha particle dose from the time of the procedure to time t has two components: one arising from the alpha decays of $^{220}$Rn and $^{216}$Po (which follows immediately at essentially the same location, due to the 0.15 s half-life of $^{216}$Po), and one arising from the alpha decay of either $^{212}$Bi (with 36% branching) or $^{212}$Po (with 64% branching). The accumulated dose may be summarized by the following equations, which depend on the values of $n_{Rn}(r,t)$, $n_{Pb}(r,t)$ and $n_{Bi}(r,t)$ calculated in solving the migration equations:

$$Dose_\alpha(RnPo; r, t) = \frac{E_\alpha(RnPo)}{\rho} \int_0^t \lambda_{Rn} n_{Rn}(r, t')dt' \tag{13}$$

$$Dose_\alpha(BiPo; r, t) = \frac{E_\alpha(BiPo)}{\rho} \int_0^t \lambda_{Bi} n_{Bi}(r, t')dt' \tag{14}$$

$E_\alpha(RnPo)=(6.29+6.78)$ MeV$=13.07$ MeV$=2.09\cdot 10^{-12}$ J is the sum of energies of the alpha particles emitted (essentially at the same location) by $^{220}$Rn and $^{216}$Po. $E_\alpha(BiPo)=7.80$ MeV$=1.25\cdot 10^{-12}$J is the average energy of the alpha particles emitted either by $^{212}$Bi or $^{212}$Po and $\rho$ is the tissue density (which, for all practical purposes, can be set to 1 g/cm$^3$). We define the asymptotic dose as the dose delivered from the time of the implanting of the sources in the tumor to infinity (in practice to ~5 half-lives of $^{224}$Ra):

$$Dose_\alpha^{asy}(RnPo; r) = \frac{E_\alpha(RnPo)}{\rho} \int_0^\infty \lambda_{Rn} n_{Rn}(r, t)dt \tag{15}$$

$$Dose_\alpha^{asy}(BiPo; r) = \frac{E_\alpha(BiPo)}{\rho} \int_0^\infty \lambda_{Bi} n_{Bi}(r, t)dt \tag{16}$$

In some embodiments, the equations are solved based on the assumption of a uniform temporal behavior of the number densities throughout the entire region surrounding the source. This assumption is referred to as "0D approximation".

The asymptotic dose contributed by $^{220}$Rn and $^{216}$Po under the 0D approximation for a point source is given by:

$$Dose_\alpha^{asy,0D}(RnPo; r) = \frac{\lambda_{Rn} P_{des}(Rn) \Gamma_{Ra}^{src}(0) E_\alpha(RnPo)}{4\pi\rho D_{Rn}} \frac{e^{-r/L_{Rn}}}{r} \tau_{Ra} \tag{17}$$

where $\tau_{Ra}=1/\lambda_{Ra}$ is the mean lifetime of $^{224}$Ra. To calculate an approximate dose up to a time t, the $Dose_\alpha^{asy,0D}$(RnPo;r) calculated in equation (17) is optionally multiplied by $$1 - e^{-\frac{t}{\tau_{Ra}}}.$$

The spatial dependence of the dose is governed by the $^{220}$Rn diffusion length:

$$L_{Rn} = \sqrt{\frac{D_{Rn}}{\lambda_{Rn} - \lambda_{Ra}}} \quad (18)$$

For the dose contributed by $^{212}$Bi and $^{212}$Po, we first define the diffusion lengths of $^{212}$Pb and $^{212}$Bi:

$$L_{Pb} = \sqrt{\frac{D_{Pb}}{\lambda_{Pb} + \alpha_{Pb} - \lambda_{Ra}}} \quad (19)$$

$$L_{Bi} = \sqrt{\frac{D_{Bi}}{\lambda_{Bi} + \alpha_{Bi} - \lambda_{Ra}}} \quad (20)$$

In some embodiments, the effective $^{212}$Pb lifetime is:

$$\tau_{Pb}^{eff} = \frac{1}{\lambda_{Pb} + \alpha_{Pb}} \quad (21)$$

This parameter is essentially a geometric average of the mean radioactive lifetime of $^{212}$Pb, $\tau_{Pb}=1/\lambda_{Pb}$ and its mean clearance time $1/\alpha_{Pb}$.

The asymptotic 0D $^{212}$Bi/$^{212}$Po alpha particle dose for a point source is given by:

$$Dose_\alpha^{asy,0D}(BiPo; r) = \quad (22)$$

$$\frac{\lambda_{Bi}E_\alpha(BiPo)}{\rho}\left(A_{Bi}\frac{e^{-r/L_{Rn}}}{r} + B_{Bi}\frac{e^{-r/L_{Pb}}}{r} + C_{Bi}\frac{e^{-r/L_{Bi}}}{r}\right)\left(\tau_{Ra} - \tau_{Pb}^{eff}\right)$$

where:

$$A_{Pb} = \left(\frac{L_{Rn}^2 L_{Pb}^2}{L_{Rn}^2 - L_{Pb}^2}\right)\frac{\lambda_{Rn}}{D_{Pb}}\frac{P_{des}(Rn)\Gamma_{Ra}^{src}(0)}{4\pi D_{Rn}} \quad (23)$$

$$B_{Pb} = \frac{(P_{des}^{eff}(Pb) - P_{des}(Rn))\Gamma_{Ra}^{src}(0)}{4\pi D_{Pb}} - A_{Pb} \quad (24)$$

$$A_{Bi} = \left(\frac{L_{Rn}^2 L_{Bi}^2}{L_{Rn}^2 - L_{Bi}^2}\right)\frac{\lambda_{Pb}}{D_{Bi}}A_{Pb} \quad (25)$$

$$B_{Bi} = \left(\frac{L_{Pb}^2 L_{Bi}^2}{L_{Pb}^2 - L_{Bi}^2}\right)\frac{\lambda_{Pb}}{D_{Bi}}B_{Pb} \quad (26)$$

$$C_{Bi} = -(A_{Bi} + B_{Bi}) \quad (27)$$

To calculate an approximate dose up to a time t, the following equation is used to calculate $Dose_\alpha^{asy,0D}$(BiPo;r) instead of equation (22):

$$Dose_\alpha^{asy,0D}(BiPo; r) = \quad (22')$$

$$\frac{\lambda_{Bi}E_\alpha(BiPo)}{\rho}\left(A_{Bi}\frac{e^{-\frac{r}{L_{Rn}}}}{r} + B_{Bi}\frac{e^{-\frac{r}{L_{Pb}}}}{r} + C_{Bi}\frac{e^{-\frac{r}{L_{Bi}}}}{r}\right)$$

$$\left(\tau_{Ra}\left(1 - e^{-\frac{t}{\tau_{Ra}}}\right) - \tau_{Pb}^{eff}\left(1 - e^{-\frac{t}{\tau_{Pb}^{eff}}}\right)\right)$$

In some embodiments the physical source can be approximated as a finite line source. In this case, the total alpha particle dose D(r,θ,t) at any point (defined by r and θ relative to the source center and axis) is obtained by dividing the source to a large number of small point-like segments and summing the contributions of $^{220}$Rn/$^{216}$Po and $^{212}$Bi/$^{212}$Pb, equations (17) and (22), from each segment, using the radial distances from the point (r,θ) to each segment.

The total radiation dose D(r,θ,t) due to alpha particles at any point is the sum of contributions by the pairs $^{220}$Rn/$^{216}$Po and $^{212}$Bi/$^{212}$Pb, equations (17) and (22).

Experimentally, it is more convenient to replace $\alpha_{Pb}$ by an equivalent parameter, namely the $^{212}$Pb leakage probability, defined as:

$$P_{leak}(Pb) = \frac{\alpha_{Pb}}{\lambda_{Pb} + \alpha_{Pb}}$$

In some embodiments, the diffusion length $L_{Pb}$ of $^{212}$Pb is measured in mice-borne tumors and accordingly the diffusion coefficient $D_{Pb}$ is set using equation (19). Measurements carried out by applicant, found values of the diffusion length $L_{Pb}$ in the range of about 0.2-0.7 millimeters. The values differ among tumor types and/or distance between the source and the tumor perimeter. The values for several types of tumors are listed in the following table.

| Tumor type | 212 Pb diffusion length in millimeters |
| --- | --- |
| Squamous cell carcinoma | 0.50 ± 0.12 |
| Colon | 0.45 ± 0.06 |
| GBM | 0.40 ± 0.09 |
| Prostate | 0.35 ± 0.05 |
| Breast (triple negative) | 0.35 ± 0.05 |
| Pancreas | 0.30 ± 0.05 |

Accordingly, in some embodiments, in calculating the radionuclide distributions, the diffusion length $L_{Pb}$ of $^{212}$Pb is given the average value in the table of the corresponding tumor type. Alternatively, the lower value of the corresponding range in the table is used. In some embodiments, for cancer types not in the table, a value smaller than 0.4 mm, smaller than 0.35 mm or even smaller than 0.3 mm is used for the diffusion length $L_{Pb}$.

Optionally, the $^{220}$Rn diffusion length is estimated in the range 0.2-0.4 mm, for example, by a value of at least 0.23 millimeters, at least 0.25 mm, or even at least 0.27 mm. In some embodiments, a value of 0.3 mm is used for the $^{220}$Rn diffusion length. Alternatively or additionally, the $^{220}$Rn diffusion length used is smaller than 0.33 mm, smaller than 0.29 millimeters or even smaller than 0.27 millimeters.

The $^{212}$Pb leakage probability is optionally estimated by a probability greater than 30% or even greater than 35%, for example 40%. Optionally, the $^{212}$Pb leakage probability is assumed to be lower than 70%, lower than 60% or even lower than 50%. In some embodiments, different values of the $^{212}$Pb leakage probability are used for different regions of the tumor. The value for regions close to the edge of the tumor is optionally greater than 70% or even greater than 80%. Deep inside the tumor, in its necrotic core, the $^{212}$Pb leakage probability can be much lower, e.g., less than 10%.

It is noted that instead of using the integration of equations (15)-(16) to calculate the radiation dose from the radionuclide distributions, other calculation methods may be used, such as Monte Carlo techniques.

Table Generation

The tables are generated from the total alpha particle dose $D(r,\theta,t)$ of each point from the beginning of the procedure (e.g., insertion of the sources to the tumor) at time $t=0$, up to time t. In some embodiments, instead of inserting the calculated radiation distribution values $D(r,\theta,t)$ directly into tables, the calculated distribution values $D(r,\theta,t)$ are converted into a form accepted by a commercially available radiation treatment planning system (TPS), which in turn generates the tables.

Optionally, the tables are generated by a treatment planning system (TPS), such as the BrachyVision TPS, which is based on the functions:

$$\dot{D}_{TPS}(r, \theta, t) = \dot{D}_{TPS}(r, \theta, 0)e^{-\lambda t}$$

$$D_{TPS}(r, \theta, t) = \int_0^{\tau} \dot{D}_{TPS}(r, \theta, t')dt' = \dot{D}_{TPS}(r, \theta, 0)\tau(1 - e^{-t/\tau}),$$

where $\tau = \dfrac{1}{\lambda}$ $$\dot{D}_{TPS}(r, \theta, 0) = Sk(0)\Lambda \frac{G_L(r, \theta)}{G_L(r_0, \theta_0)} g_L(r)F(r, \theta)$$

and requires user setting of the functions $g_L(r)$ and $F(r, \theta)$, an activity level of the sources, a dose rate constant $\Lambda$ per table, and a value $f_{ak}$, which is a conversion factor between activity and Air Kerma Strength. This formalism is described, for example, in the TG-43 publication mentioned in the background section, and which is incorporated herein by reference in its entirety. It is noted that such a TPS is not designed for alpha radiation.

In accordance with some embodiments, the value of $f_{ak}$ is set arbitrarily, for example to 1, and the $g_L(r)$ and $F(r, \theta)$ functions are calculated for a given time t from the DaRT radiation distribution values $D(r,\theta,t)$ as:

$$g_L^{(t)}(r) = \frac{D(r, \theta_0, t)}{D(r_0, \theta_0, t)} \frac{G_L(r_0, \theta_0)}{G_L(r, \theta_0)}$$

$$F^{(t)}(r, \theta) = \frac{D(r, \theta, t)}{D(r, \theta_0, t)} \frac{G_L(r, \theta_0)}{G_L(r, \theta)}$$

where $G_L(\,)$ is a general closed-form geometrical function, which depends on the source length L and is already programmed in the TPS. The parameters $r_0$ and $\theta_0$ represent a particular reference point (e.g., $r_0=1$ cm and $\theta_0=90°$). The dose rate constant $\Lambda$ is assigned for each table a calibration value suitable for that table. Note that unlike conventional brachytherapy sources, the functions $F(\,)$ and $g_L(\,)$ for DaRT depend on the duration of the treatment t, because of temporal changes in the spatial shape of the number densities of the diffusing atoms.

For cases in which the TPS limits the value of $F(\,)$, instead of using $F(\,)$, a normalized $$F_{norm} = \frac{F(r, \theta)}{Fmax}$$

is used, where Fmax is selected as a highest value of the function $F(\,)$, or a sufficient value which prevents $F_{norm}$ from going beyond the bounds allowed by the TPS. The value of $F_{max}$ is optionally compensated for, if not internally compensated for by the TPS, in setting the TPS system coefficient $\Lambda_{TPS}=\Lambda F_{max}$.

Optionally, $r_0$ is selected to prevent $g(r)$ from going out the bounds of the values allowed by the TPS. The values of $Sk(0),\Lambda$ are optionally selected such that $$Sk(0)\Lambda = \frac{D(r_0, \theta_0, t)}{\tau(1 - e^{-t/\tau_{Ra}})},$$

where $\tau_{Ra}$ is the mean lifetime of $^{224}$Ra.

Electron and Photon Radiation

In some embodiments, separate tables are prepared for the alpha radiation and for the electron and photon radiation. In calculating the radiation dose distribution, separate calculations are performed for the alpha radiation by accessing alpha radiation tables and for the electron and photon radiation by accessing suitable tables and then the results are combined. Optionally, the electron and/or photon radiation tables provide accumulated dose values, as provided by the alpha-radiation tables. Alternatively, the electron and/or photon radiation tables provide dose rate values, as in the TG-43 publication mentioned above.

Alternatively, a single table is used for the alpha, electron and photon radiation. Optionally, in accordance with this alternative, in summing the alpha, electron and/or photon radiation, the alpha radiation value or the electron and/or photon radiation value is multiplied by user provided relative biological effectiveness (RBE) factors, determined using any suitable method known in the art, which take into account the different biological effects of the alpha and electron and/or photon radiation. RBE values for alpha particles depend on the type of the tumor, and are typically in the range 3-5. For electrons and photons RBE values are typically 1 at high energy (above a few hundred keV), but become larger than 1 at lower energies.

Optionally, in calculating the electron and/or radiation dose, for simplicity, the radionuclides are all assumed to be located on the source, and the migration of radionuclides in the tumor is ignored. This assumption was found to have only a small effect on the results, because of the long range of electrons and large mean free path of gamma and x-ray photons relative to the migration scale, governed by the diffusion lengths. In some embodiments, however, the electron and/or photon radiation dose calculation does take into account the early removal of radionuclides through the blood stream, for example by reducing the number of $^{212}$Pb radionuclides in the tumor by the $^{212}$Pb leakage probability.

Optionally, the electron and photon radiation dose is calculated by Monte Carlo techniques (e.g., using the EGS, FLUKA, GEANT4, MCNP or track structure codes), for the entire spectrum of emitted radiation by $^{224}$Ra and its daughters. Optionally, for simplicity, the medium is assumed to be water. Alternatively, other calculation methods are used, such as model based dose calculation algorithms (MBDCAs).

Alternatives

In the above description, the tumor is considered to have the same parameters throughout its volume. In other embodiments, the tumor is considered to have different parameter values in different areas. Optionally, separate tables are generated for different distances of the sources from an edge of the tumor. For example, separate calculations are performed for sources in a range up to 2 millimeters from an edge of the tumor, between 2-4 millimeters from the edge of the tumor, between 4-6 millimeters from the edge of the tumor, and above 6 millimeters from the edge of the tumor. In other embodiments, more than 4 ranges of distances of sources from an edge of the tumor are used, and/or ranges of coarser granularities than 2 millimeters, or finer granularities than 2 millimeters, are used.

For each of the ranges, separate values are provided for the tumor parameters. For example, a higher lead-212 leakage probability (and/or a shorter diffusion length) is assigned to areas closer to the tumor edge, as the leakage is higher at the edges of the tumor. In using the tables, for each source a corresponding one of the tables is selected according to the location of the source in the tumor.

The distance between the source and the edge of the tumor is optionally measured from the closest point on the source to the closest point on the edge of the tumor. Alternatively, the distance is measured from the center of the source. Further alternatively the distance is measured as an average distance along the length of the source or an average between the two ends of the source. In other embodiments, in addition to the distance, a measure of an orientation of the source, such as an angle between the source axis and a shortest line connecting the center of the source to an edge of the tumor is used in dividing the tumor into separate zones.

As described above, the same tumor parameters, e.g., diffusion length, are used for the entire duration of the treatment. In other embodiments, however, in the calculation of the radiation dose, one or more of the tumor parameters, such as the diffusion lengths, are changed with the time since the beginning of the treatment, due to the death of cells because of the treatment, which changes the properties of the tumor. It is noted that these embodiments will have a larger effect on calculations of the dose during longer term periods, than during short term durations in which the parameters of the tumor change very little or not at all.

Alternatively to using tables, the above calculation methods are used directly for calculation of the radiation dose distribution.

CONCLUSION

It will be appreciated that the above described methods and apparatus are to be interpreted as including apparatus for carrying out the methods and methods of using the apparatus. It should be understood that features and/or steps described with respect to one embodiment may sometimes be used with other embodiments and that not all embodiments of the invention have all of the features and/or steps shown in a particular figure or described with respect to one of the specific embodiments. Tasks are not necessarily performed in the exact order described.

It is noted that some of the above described embodiments may include structure, acts or details of structures and acts that may not be essential to the invention and which are described as examples. Structure and acts described herein are replaceable by equivalents which perform the same function, even if the structure or acts are different, as known in the art. The embodiments described above are cited by way of example, and the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art. Therefore, the scope of the invention is limited only by the elements and limitations as used in the claims, wherein the terms "comprise," "include," "have" and their conjugates, shall mean, when used in the claims, "including but not necessarily limited to."

The invention claimed is:

1. Apparatus for planning a diffusing alpha-emitter radiation therapy (DaRT) treatment session, comprising:
   an output interface;
   a memory configured with a plurality of first tables which provide an accumulated measure of radiation over a specific time period, due to one or more types of DaRT radiotherapy sources which emit daughter radionuclides, for a plurality of different distances and angles relative to the DaRT radiotherapy sources; and
   a processor configured to receive a description of a layout of the DaRT radiotherapy sources in a tumor, to calculate a radiation dose distribution in the tumor responsive to the layout, using the first tables in the memory, and to output feedback for the DaRT treatment session responsive to the radiation dose distribution, through the output interface,
   wherein the accumulated measure of radiation provided by the first tables comprises an accumulated radiation dose due only to alpha radiation.

2. The apparatus of claim 1, wherein the memory is additionally configured with a plurality of second tables for different time periods for a single source type, and wherein the processor is configured to determine a treatment duration of the layout, and to select a table from the second tables to be used in calculating the radiation dose distribution responsive to the treatment duration.

3. The apparatus of claim 1, wherein the memory is additionally configured with a plurality of second tables for a single source type in different zones of the tumor, and wherein the processor is configured to select a table from the second tables to be used in calculating the radiation dose distribution from each DaRT radiotherapy source in the layout, responsive to a zone from the different zones in which each DaRT radiotherapy source is located.

4. The apparatus of claim 3, wherein the processor determines the zone in which each DaRT radiotherapy source is located responsive to a distance between the DaRT radiotherapy source and an edge of the tumor.

5. The apparatus of claim 1, wherein the processor is configured to identify areas of the tumor having in the calculated radiation dose distribution a radiation dose below a threshold and to suggest changes to the layout which bring the radiation dose in the identified areas to above the threshold.

6. The apparatus of claim 1, wherein the processor is configured to repeat the calculation of a radiation dose distribution for a plurality of different treatment durations and to select one of the durations responsive to the calculations.

7. The apparatus of claim 1, wherein the accumulated measure of radiation provided by the first tables comprises one or more number densities of the radionuclides.

8. Apparatus for planning a diffusing alpha-emitter radiation therapy (DaRT) treatment session, comprising:
an output interface;
a memory configured with a plurality of first tables which provide an accumulated measure of radiation over a specific time period, due to one or more types of DaRT radiotherapy sources which emit daughter radionuclides, for a plurality of different distances and angles relative to the DaRT radiotherapy sources; and
a processor configured to receive a description of a layout of the DaRT radiotherapy sources in a tumor, to calculate a radiation dose distribution in the tumor responsive to the layout, using the first tables in the memory, and to output feedback for the DaRT treatment session responsive to the radiation dose distribution, through the output interface,
wherein the accumulated measure of radiation provided by the first tables comprises an accumulated radiation dose due to alpha radiation and one or more of electron and photon radiation.

9. A method of providing a radiotherapy treatment session, comprising:
receiving, by a processor, a plurality of parameters of tissue of a tumor requiring radiotherapy;
receiving, by the processor, an indication of a layout of diffusing alpha-emitter radiation therapy (DaRT) sources to be placed in the tumor;
calculating a distribution of radon-220, lead-212 and bismuth-212 radionuclides in the tumor, responsive to the layout of sources;
determining a first radiation dose distribution resulting from alpha radiation emitted in the tumor, responsive to the calculated distribution;
determining a second radiation dose distribution resulting from electron and photon radiation in the tumor, responsive to the layout of sources;
setting one or more parameters of the radiotherapy treatment session responsive to the determined first and second radiation dose distributions; and
inserting the DaRT sources of the layout into the tumor, responsive to the set one or more parameters,
wherein calculating the distribution of radon-220, lead-212, and bismuth-212 is performed as a function of diffusion coefficients of radon-220 and lead-212 in the tumor.

10. The method of claim 9 wherein calculating the distribution of radon-220, lead-212, and bismuth-212 is performed by solving a migration equation of lead-212 including a leakage factor which is a product of a concentration of lead-212 and a constant.

11. The method of claim 9, wherein calculating the distribution of the radionuclides comprises calculating a distribution of the radionuclides for a single source of the sources in the layout and summing the calculated distribution of the radionuclides for the single source, for all of the sources in the layout.

12. The method of claim 9, wherein the setting one or more parameters of the radiotherapy treatment session comprises selecting an activity of the sources in the layout.

13. The method of claim 9, wherein the setting one or more parameters of the radiotherapy treatment session comprises adjusting the layout of the sources.

14. The method of claim 9, wherein calculating the distribution of radionuclides in the tumor and determining the first radiation dose distribution comprises repeating the calculating of the distribution of radionuclides and the determining of the first radiation dose distribution for a plurality of different durations, and wherein setting one or more parameters of the radiotherapy treatment session comprises selecting a duration of the treatment session responsive to the repeated calculating and determining.

15. The method of claim 9, wherein receiving the indication of the layout comprises receiving an image of the tumor with the sources therein and determining locations of the sources in the tumor responsive to the image.

16. The method of claim 9, wherein determining the second radiation dose distribution is performed in a manner that does not depend on the distribution of radon-220, lead-212, and bismuth-212 in the tumor.

17. A method of providing a radiotherapy treatment session, comprising:
receiving, by a processor, a plurality of parameters of tissue of a tumor requiring radiotherapy;
receiving, by the processor, an indication of a layout of diffusing alpha-emitter radiation therapy (DaRT) sources to be placed in the tumor;
calculating a distribution of radon-220, lead-212 and bismuth-212 radionuclides in the tumor, responsive to the layout of sources;
determining a first radiation dose distribution resulting from alpha radiation emitted in the tumor, responsive to the calculated distribution;
determining a second radiation dose distribution resulting from electron and photon radiation in the tumor, responsive to the layout of sources;
setting one or more parameters of the radiotherapy treatment session responsive to the determined first and second radiation dose distributions; and
inserting the DaRT sources of the layout into the tumor, responsive to the set one or more parameters,
wherein calculating the distribution of radon-220, Lead-212, and bismuth-212 in the tumor and determining the first radiation dose distribution comprises preparing in advance tables of radiation distributions for a plurality of different tumor types and determining the first radiation dose distribution by summing values matching the layout, from one of the tables.

18. The method of claim 17, wherein preparing in advance tables of radiation distributions comprises preparing for each of the tumor types, a plurality of tables for respective treatment durations.

19. The method of claim 18, wherein the treatment durations for which the tables are prepared, are unevenly distributed over a duration of effectiveness of the sources of the layout.

20. A method of providing a radiotherapy treatment session, comprising:
receiving, by a processor, a plurality of parameters of tissue of a tumor requiring radiotherapy;
receiving, by the processor, an indication of a layout of diffusing alpha-emitter radiation therapy (DaRT) sources to be placed in the tumor;
calculating a distribution of radon-220, lead-212 and bismuth-212 radionuclides in the tumor, responsive to the layout of sources;
determining a first radiation dose distribution resulting from alpha radiation emitted in the tumor, responsive to the calculated distribution;
determining a second radiation dose distribution resulting from electron and photon radiation in the tumor, responsive to the layout of sources;

setting one or more parameters of the radiotherapy treatment session responsive to the determined first and second radiation dose distributions; and inserting the DaRT sources of the layout into the tumor, responsive to the set one or more parameters, wherein calculating the distribution of radon-220, lead-212, and bismuth-212 radionuclides comprises calculating based on at least one equation which depends on a diffusion coefficient of lead-212, and wherein the value of the diffusion coefficient of lead-212 is calculated as a function of a diffusion length of lead-212.

21. The method of claim 20, wherein the diffusion length of lead-212 is assigned a value in a range of 0.2-0.4 millimeters.

22. The method of claim 20, wherein the diffusion length of lead-212 is assigned a value dependent on a tissue type of the tumor.

23. A method of providing a radiotherapy treatment session, comprising:

receiving, by a processor, a plurality of parameters of tissue of a tumor requiring radiotherapy;

receiving, by the processor, an indication of a layout of diffusing alpha-emitter radiation therapy (DaRT) sources to be placed in the tumor;

calculating a distribution of radon-220, lead-212 and bismuth-212 radionuclides in the tumor, responsive to the layout of sources;

determining a first radiation dose distribution resulting from alpha radiation emitted in the tumor, responsive to the calculated distribution;

determining a second radiation dose distribution resulting from electron and photon radiation in the tumor, responsive to the layout of sources;

setting one or more parameters of the radiotherapy treatment session responsive to the determined first and second radiation dose distributions; and inserting the DaRT sources of the layout into the tumor, responsive to the set one or more parameters, wherein calculating the distribution of radon-220, lead-212, and bismuth-212 is performed by solving a migration equation of lead-212 including a leakage factor which is a product of a concentration of lead-212 and a constant.

24. A method of providing a radiotherapy treatment session, comprising:

receiving, by a processor, a plurality of parameters of tissue of a tumor requiring radiotherapy;

receiving, by the processor, an indication of a layout of diffusing alpha-emitter radiation therapy (DaRT) sources to be placed in the tumor;

calculating a distribution of radon-220, lead-212 and bismuth-212 radionuclides in the tumor, responsive to the layout of sources;

determining a first radiation dose distribution resulting from alpha radiation emitted in the tumor, responsive to the calculated distribution;

determining a second radiation dose distribution resulting from electron and photon radiation in the tumor, responsive to the layout of sources;

setting one or more parameters of the radiotherapy treatment session responsive to the determined first and second radiation dose distributions; and inserting the DaRT sources of the layout into the tumor, responsive to the set one or more parameters, wherein determining the second radiation dose distribution, is performed in a manner ignoring the distribution of radon-220, lead-212, and bismuth-212 in the tumor.

* * * * *